US009427518B2

(12) United States Patent
Brueckner

(10) Patent No.: US 9,427,518 B2
(45) Date of Patent: Aug. 30, 2016

(54) PUMP ROTOR

(75) Inventor: Christoph Brueckner, Geldersheim (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 568 days.

(21) Appl. No.: 13/313,241

(22) Filed: Dec. 7, 2011

(65) Prior Publication Data

US 2012/0148415 A1  Jun. 14, 2012

Related U.S. Application Data

(60) Provisional application No. 61/421,288, filed on Dec. 9, 2010.

(30) Foreign Application Priority Data

Dec. 9, 2010  (DE) .................. 10 2010 053 903

(51) Int. Cl.
*F04B 43/12* (2006.01)
*A61M 5/142* (2006.01)

(52) U.S. Cl.
CPC ...... *A61M 5/14232* (2013.01); *F04B 43/1253* (2013.01); *F04B 43/1276* (2013.01); *F04B 43/1292* (2013.01)

(58) Field of Classification Search
CPC .................. F04B 43/1253; F04B 43/1276
USPC ................ 417/477.7, 477.11, 477.8
See application file for complete search history.

(56) References Cited

U.S. PATENT DOCUMENTS

| 3,822,948 | A | * | 7/1974 | Handl | 401/146 |
|---|---|---|---|---|---|
| 4,375,346 | A | * | 3/1983 | Kraus et al. | 417/388 |
| 4,720,249 | A | | 1/1988 | Krebs et al. | |
| 5,009,573 | A | * | 4/1991 | Ring et al. | 417/53 |
| 5,033,942 | A | * | 7/1991 | Petersen | 417/475 |
| 5,462,417 | A | * | 10/1995 | Chapman | 417/477.7 |
| 6,036,459 | A | * | 3/2000 | Robinson | 417/477.7 |
| 7,300,264 | B2 | * | 11/2007 | Souza | 417/477.11 |
| 2002/0064470 | A1 | * | 5/2002 | Andersen et al. | 417/477.3 |
| 2005/0053502 | A1 | * | 3/2005 | Souza | 417/477.11 |
| 2007/0217932 | A1 | * | 9/2007 | Voyeux et al. | 417/477.2 |

FOREIGN PATENT DOCUMENTS

| DE | 2539511 A1 | 3/1976 |
|---|---|---|
| DE | 2452771 A1 | 5/1976 |
| DE | 3326785 A1 | 2/1985 |

(Continued)

OTHER PUBLICATIONS

PCT International Search Report and Written Opinion from PCT/EP2011/006153 mailed on Jul. 20, 2012.

(Continued)

*Primary Examiner* — Peter J Bertheaud
(74) *Attorney, Agent, or Firm* — Kenyon & Kenyon LLP

(57) ABSTRACT

The present invention relates to a pump rotor for a peristaltic hose pump, in particular a medical peristaltic hose pump, with at least one actuating device, by which the pump rotor can be actuated hydraulically and/or pneumatically. Furthermore the present invention in particular relates to a medical peristaltic hose pump and to a method for actuating a pump rotor of a peristaltic hose pump.

7 Claims, 2 Drawing Sheets

(56) References Cited

FOREIGN PATENT DOCUMENTS

| FR | 2 284 783 A1 | 4/1976 |
|----|--------------|--------|
| WO | 95/17597 A1  | 6/1995 |

OTHER PUBLICATIONS

Office Action from German Patent Application No. 10 2010 053 903.1 mailed on Oct. 13, 2011.

* cited by examiner

PUMP ROTOR

CROSS REFERENCE TO RELATED APPLICATIONS

This application claims priority to U.S. Provisional Application No. 61/421,288 filed Dec. 9, 2010 and to German Patent Application No. 10 2010 053 903.1 filed on Dec. 9, 2010, both of which are incorporated fully by reference herein.

FIELD OF THE INVENTION

The present invention relates to a pump rotor for a peristaltic hose pump, in particular a medical peristaltic hose pump. Furthermore the present invention in particular relates to a medical peristaltic hose pump and to a method for actuating a pump rotor of a peristaltic hose pump.

BACKGROUND OF THE INVENTION

From the prior art, peristaltic hose pumps are known, in which the rollers which occlude the inserted hose are resiliently mounted. The spring force in dependence on the compliance of the inserted hose determines the maximum afterpump pressure, at which an occlusion of the pump still exists.

Such peristaltic hose pump for example is known from DE 33 26 785 A1. Accordingly, in a pump rotor for peristaltically operating roller pumps, in particular for hose pumps in medical engineering, two roller carriers are in drive connection by means of two lever rods and two springs and are controlled such that the rollers rolling on a pump hose on the one hand are running on a rolling circle with constant diameter and on the other hand are able to independently adjust to pump hoses with different wall thicknesses or diameters.

In the case of a stenosis downstream of the pump, the pump pressure is limited to safe values and the hose bursting or a succeeding filter, such as a dialysis filter, being damaged is prevented. In addition, a patient whose blood, for example in connection with a dialysis treatment, is delivered for the dialysis by means of such peristaltic hose pump in an extracorporeal blood circuit, can be prevented from being put in danger at a later time.

The required spring constant with which the rollers are pressed against the inserted hose is dependent on the chosen type of treatment, the inserted hose and the succeeding filter and thus is variable.

In the peristaltic hose pumps known from the prior art, changed requirements concerning the spring force by means of which the rollers are pressed against the hose inserted into the peristaltic hose pump can only be realized by a replacement of the spring, which often is equivalent to a replacement of the rotor. However, this is comparatively expensive. In addition, the gradations of the spring force generally are not arbitrarily small, so that it is not possible to actually adjust to any desired force, but possibly required adaptation of the occlusion force.

In addition, during the assembly and disassembly of the pump with the hose, manual force must be applied in addition, in order to compress the rollers to such an extent that the hose can also be inserted into the pump bed.

SUMMARY OF THE INVENTION

Therefore, it is the object of the present invention to develop a pump rotor and a peristaltic hose pump as mentioned above in an advantageous way, in particular to the effect that an easier and faster adjustment of the pressing and/or compression force of the peristaltic hose pump to be exerted on a hose inserted into the peristaltic hose pump can be made possible.

In accordance with the invention, this object is solved by a pump rotor with the features as described herein. Accordingly, it is provided that a pump rotor for a peristaltic hose pump is provided with at least one actuating means, by means of which the pump rotor can be actuated hydraulically and/or pneumatically. The peristaltic hose pump in particular can be a medical peristaltic hose pump, i.e. a peristaltically operating pump. Such pumps can be used in particular as blood pumps e.g. in an extracorporeal blood circuit of a dialysis treatment system. In principle, it is also conceivable to use such peristaltic hose pumps on the water side and/or in the water part of a dialysis treatment system, i.e. for delivering the dialysate and/or the components of the dialysate on the dialysate side of the dialysis treatment system.

The use of an actuating means, by means of which the pump motor can be actuated hydraulically and/or pneumatically, in particular involves the advantage that the degree of adjustment possibilities is increased, in particular due to the fact that a stepless actuation by the actuating means is possible due to the hydraulic and/or pneumatic actuation of the pump rotor. This represents an essential difference and also involves an advantage as compared to the previous use of springs, where it is, however, also conceivable to still use springs in addition to the hydraulic and/or pneumatic actuation of the pump rotor.

Furthermore, it can be provided that the pump rotor includes at least one rotor roller, which can be moved by means of the actuating means, in particular be retracted and/or extended. It is also possible to be able to retract, but also extend the rotor roller hydraulically and/or pneumatically in an advantageous way. In this way, it advantageously becomes possible to be able to adjust the position of the rotor roller with high accuracy.

Furthermore, it is possible that by hydraulically and/or pneumatically moving the pump rotor by means of the rotor roller onto a hose inserted into the peristaltic hose pump a pressing and/or compression force can be generated and/or be adjusted. Since due to the advantageous stepless and highly accurate positionability of the rotor roller by means of the hydraulic and/or pneumatic actuating means the position of the rotor roller relative to the hose pump bed also is adjustable, the occlusion can thereby be adjusted with high accuracy. The pressing and/or compression force to be exerted on the hose inserted into the peristaltic hose pump by means of the rotor roller thus is adjustable in a variable and stepless manner.

The pressing and/or compression force acting on the hose inserted into the peristaltic hose pump can also be referred to as occlusion force.

In particular, it can be provided that at least one control and/or regulating means is provided and that the pressing and/or compression force can be controlled and/or regulated in a variable and/or process-controlled and/or process-regulated manner by means of the control and/or regulating means, in particular by taking into account the factors of the hose inserted into the peristaltic hose pump, of the type of operation and use of the peristaltic hose pump and/or of the used components such as a dialysis filter as part of an extracorporeal blood circuit, which is operated with the peristaltic hose pump. Now, it is advantageously possible to react to changed requirements concerning the aforementioned pressing and/or compression force promptly and appropriate to the situation, without having to partly disassemble the peristaltic hose pump. In an advantageous aspect, this can now be effected semi-automatically or automatically by means of the control and/or regulating means. In an automatic control and/or regulation with reference to predefined specifications, adaptations of the pressing and/or compression force thus can be made. In a semi-automatic control and/or regulation it is conceivable, for example, that alternatively or in addition, inputs of the operators of the peristaltic hose pump can be taken into account.

Furthermore, it is possible that the actuating means is and/or comprises a pneumatic and/or hydraulic actuator, particularly preferably a pneumatic and/or hydraulic cylinder. It can be provided that the rotor roller is directly and/or indirectly attached or mounted to the piston of the pneumatic and/or hydraulic cylinder. However, it can just as well be provided that the rotor roller is directly and/or indirectly attached to the pneumatic and/or hydraulic cylinder itself and that the piston of the pneumatic and/or hydraulic cylinder is directly and/or indirectly attached to the pump rotor.

In addition, it can be provided that the actuating means is a double-acting actuating means, wherein the double-acting actuating means preferably is and/or comprises a double-acting hydraulic cylinder or hydraulic piston which is actively movable in a first and in a second direction, in particular is actively movable in a first and in a second direction by means of a hydraulically and/or pneumatically generated positive pressure. In this advantageous embodiment so-called double-acting pistons are used, to which a hydraulically and/or pneumatically generated pressure can be applied on both sides of the piston. Thus, the piston can actively be moved in both directions by corresponding valve control means. This design for example involves the advantage that only a positive pressure is required. A pneumatic design in particular involves the advantage that the positive air pressure, which mostly is present anyway in a superordinate machine, such as a dialysis machine, can easily be used.

In addition, it is possible that the actuating means is an actuating means to be actuated by means of positive pressure and negative pressure, wherein the actuating means is movable in a first direction by means of positive pressure and is movable in a second direction by means of negative pressure. When a negative pressure exists or when there is a possibility for generating a negative pressure, a forward and backward movement of the pump rotor advantageously can also be realized by applying a positive and/or negative pressure on one side of the piston.

Due to the now possible active backward movement of the rollers of the peristaltic hose pump, which are arranged and mounted on the pump rotor, wherein the active movability of the rollers is achieved by means of positive pressure or by a combination of positive and negative pressure, inserting the hose into the pump bed of the peristaltic hose pump now is also facilitated considerably.

Furthermore, the present invention relates to an actuating means. Accordingly, it is provided that an actuating means by means of which a pump rotor of a peristaltic hose pump can be actuated hydraulically and/or pneumatically is designed with the actuating means features described herein. Preferably, it is provided that the actuating means is and/or comprises a pneumatic and/or hydraulic actuator, wherein particularly preferably the pneumatic and/or hydraulic actuator is a pneumatic and/or hydraulic cylinder.

Furthermore, the present invention relates to a peristaltic hose pump. Accordingly, it is provided that a peristaltic hose pump is provided with at least one pump rotor and/or with at least one actuating means.

In addition, the present invention relates to a blood treatment machine. Accordingly, it is provided that a blood treatment machine is provided with at least one pump rotor \ and/or with at least one peristaltic hose pump, wherein the blood treatment machine preferably is a dialysis machine.

In addition, the present invention relates to a method for actuating a pump rotor of a peristaltic hose pump. It is provided that in a method for actuating a pump rotor of a peristaltic hose pump, in particular for adjusting the occlusion pressure and/or the position of the rotor rollers of a peristaltic hose pump, the pump rotor of the peristaltic hose pump is actuated hydraulically and/or pneumatically. The force which acts on the pump hose is a quantity which limits the fluid pressure downstream of the pump. The maximally possible fluid pressure downstream of the pump also is referred to as occlusion pressure. The occlusion pressure is a safety-relevant quantity when designing e.g. blood pumps for the dialysis. In the case of a stenosis downstream of the blood pump, e.g. due to clogging of the dialysis filter which is disposed downstream of the blood pump in a hemodialysis machine, the flow resistance for the blood greatly increases between the blood pump and the dialysis filter. Due to the occluding delivery of the blood pump designed as peristaltic hose pump, the fluid pressure downstream of the blood pump consequently also greatly increases, whereby a destruction of the blood cells, i.e. a hemolysis, can occur. In addition, high fluid pressures downstream of the blood pump can lead to a destruction of the blood hose or of the hollow fibers of the dialysis filter, which is dangerous to the health of the patient. Therefore it is safety-relevant to limit the fluid pressure downstream of the blood pump.

Furthermore, it can be provided that the pump rotor includes at least one rotor roller, which can be moved, in particular be retracted and/or extended, hydraulically and/or pneumatically.

In addition, it can be provided that by hydraulically and/or pneumatically moving the pump rotor by means of the rotor roller onto a hose inserted in the peristaltic hose pump a pressing and/or compression force is generated.

In particular, it is conceivable that the pressing and/or compression force can be controlled and/or regulated in a variable and/or process-controlled and/or process-regulated manner, in particular by taking into account the hose inserted into the peristaltic hose pump, the type of operation and use of the peristaltic hose pump and/or the used components such as a dialysis filter as part of an extracorporeal blood circuit, which is operated with the peristaltic hose pump.

In addition, it is possible that hydraulically and/or pneumatically moving the pump rotor in a first and in a second direction is effected actively by means of a hydraulically and/or pneumatically generated positive pressure.

It is also conceivable that the hydraulic and/or pneumatic movement of the pump rotor in a first and in a second direction is effected by means of positive pressure in a first direction and by means of negative pressure in a second direction. The first direction can be the direction of extension and the second direction can be the direction of retraction.

Furthermore it can be provided that moving is performed by using at least one pump rotor and/or at least one peristaltic hose pump and/or at least one blood treatment machine.

In addition, the present invention relates to the use of a pneumatic and/or hydraulic actuator for adjusting the occlusion pressure of a peristaltic hose pump.

Accordingly, it is provided that a pneumatic and/or hydraulic actuator is used for adjusting the occlusion pressure of a peristaltic hose pump, wherein the pneumatic and/or hydraulic actuator preferably is an actuating means and/or wherein the peristaltic hose pump preferably is a peristaltic hose pump.

BRIEF DESCRIPTION OF THE DRAWINGS

Further details and advantages of the invention will now be explained in detail with reference to an embodiment illustrated in the drawing, in which.

DETAILED DESCRIPTION OF THE DRAWINGS

Figure 1:
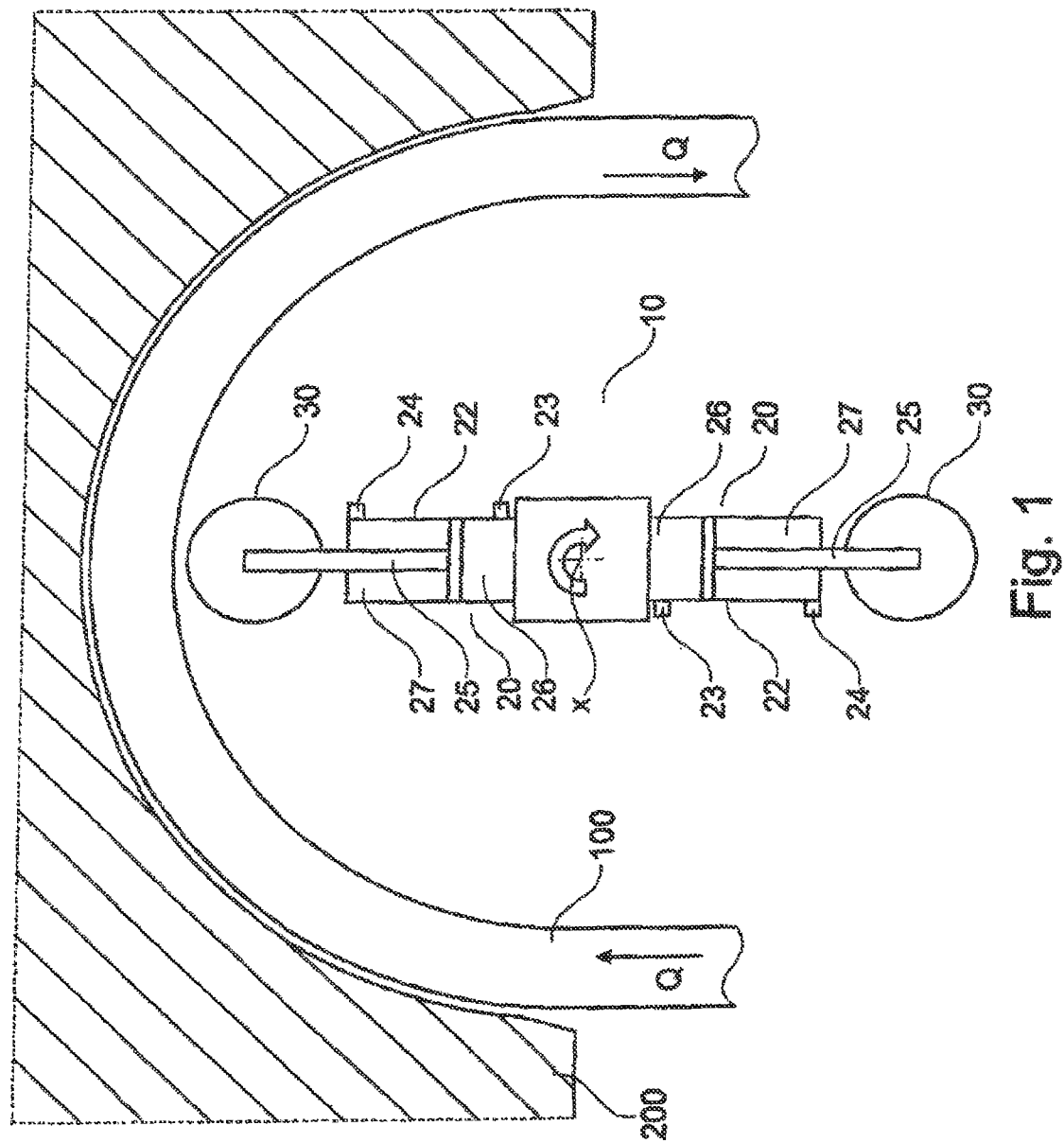
FIG. 1 shows an embodiment of the peristaltic hose pump of the invention with retracted rotor.

FIG. 1 shows a pump rotor 10 of a peristaltic hose pump for medical applications. Such medical applications include in particular dialysis treatments, wherein such a peristaltic hose pump preferably is part of a dialysis treatment device. The dialysis treatment device preferably is a dialysis machine which can be equipped for carrying out hemodialysis, hemofiltration or hemodiafiltration. It is clear to the skilled person that the inventive pump rotor 10 of a peristaltic hose pump can be used without limitation in any device in which a fluid is delivered through a peristaltic hose pump. Examples for this include devices for the automatic peritoneal dialysis, devices for plasmapheresis, infusion apparatuses or the like. The fluid delivered preferably is blood, but it can be any fluid, in particular any medical fluid, such as dialysis fluid or infusion fluids.

The peristaltic hose pump includes a pump bed 200 into which the hose 100 is inserted, wherein the fluid delivered in the hose 100 is delivered in delivery direction Q.

This is already illustrated correspondingly in FIG. 1, wherein FIG. 1 however shows a situation in which the rotor roller 30 does not yet touch the hose 100. This corresponds to the situation of the assembly or disassembly of the peristaltic hose pump. As is shown and easily understandable with reference to FIG. 1, it is easily possible in a very simple way to considerably facilitate the assembly and/or disassembly by means of the peristaltic hose pump with the pump rotor 10. When carrying out the method for actuating a pump rotor it can therefore be provided that automatically or semi-automatically, for example in response to a user input, retracting the rotor roller 30 for easier insertion of the hose 100 into the pump bed 200, followed by extending the rotor roller 30, is performed in connection with the assembly. This can be effected correspondingly during disassembly, namely in such a way that retracting the rotor roller 30 for easier removal of the hose 100 from the pump bed 200, possibly followed by an at least partial, renewed extension of the rotor roller 30 into a so-called parking position, is performed in connection with the disassembly. It can also be provided that in connection with the disassembly only an automatic or semi-automatic retraction of the rotor roller 30 is effected, in order to release the hose 100 in the pump bed 200 and provide for an easier removal of the hose 100.

Figure 2:
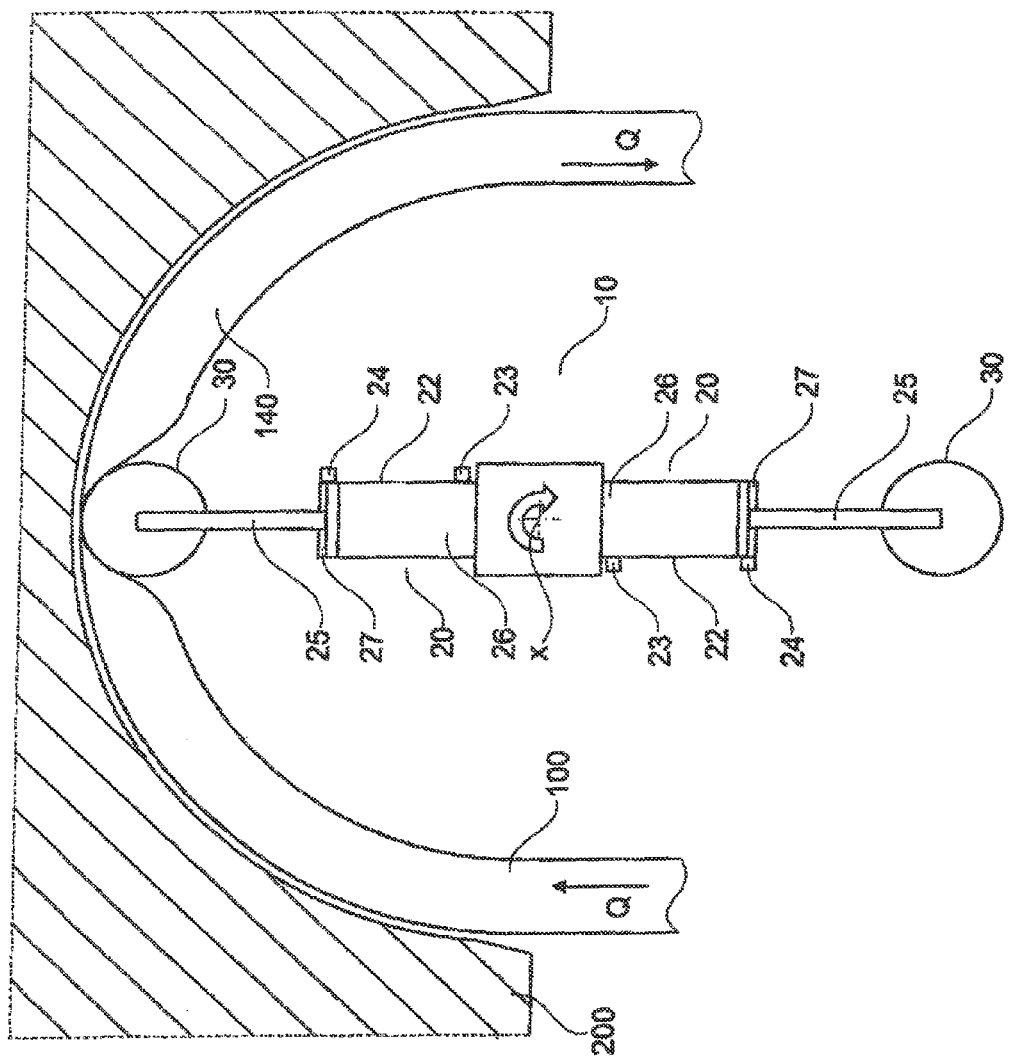
FIG. 2 shows the peristaltic hose pump of the invention with extended rotor.

The pump rotor 10 rotates for delivering the fluid, in particular the blood contained in the hose 100, in delivery direction Q about the axis of rotation x, here shown rotating in clockwise direction, and with the rotor rollers 30 it urges the hose 100 inserted into the peristaltic hose pump against the pump bed 200 of the peristaltic hose pump such that the hose is occluded in the region of the rotor rollers, as is shown in FIG. 2. Due to the rotary movement of the pump rotor 10, a delivery of the fluid 100 is effected in delivery direction Q.

In accordance with an embodiment of the invention, the two-arm pump rotor 10 with two rotor rollers 30 here includes two actuating means 20, by means of which one rotor roller 30 each can be actuated pneumatically.

In principle, it can also be provided that the actuating means 20 is a hydraulic cylinder 22, by means of which the rotor rollers 30 can be pushed in and out hydraulically.

The embodiment shown in FIGS. 1 and 2, however, represents the actuating means 20 by means of which the rotor roller 30 can be pushed in and out, in order to actuate pneumatic cylinders 22 which are connected with corresponding supply lines via the ports 23 and 24.

The ports 23 and 24 can also be connected with a corresponding valve controller.

With such a pneumatic valve controller, which is not shown in detail in FIGS. 1 and 2, it is possible for example to be able to supply compressed air to both sides of the piston 25, which is designed as a double-acting pneumatic piston. For example, when pressurizing the piston 25 via the chamber 26 or the piston space 26, which is connected with a positive pressure line via the port 23, the piston 25 can be pushed out. The rotor roller 30 thereby is pressed more strongly against the hose 100 and the pump bed 200, whereby the occlusion force is increased. It is also possible to again retract the piston 25 by pressurizing the piston via the positive pressure line connected to the port 24 and by increasing the pressure in the annular space 27 and thereby reduce the occlusion force and/or retract the rotor roller 30 for example for easier insertion of the hose. Due to such double-acting piston, the piston 25 thus can actively be charged with compressed air in both directions, i.e. in direction of refraction and extension. The required positive air pressure advantageously is provided by the superordinate machine, here a dialysis machine.

By applying a certain positive pressure in the piston space 26 opposite the annular space 27, the rotor roller 30 is moved against the hose 100 with a certain force, whereby said hose is occludingly pressed against the pump bed 200. This is shown in FIG. 2, and it should be noted in addition that the hose 100 has a non-illustrated wall thickness, which is not taken into account in FIG. 2, which in so far only shows a schematic representation.

The hose portion 140 is located downstream of the rotor roller 30 and for example is connected with a dialysis filter not shown in FIG. 1 or 2. The fluid pressure in this hose portion 140 is dependent on the flow resistance obtained here and acts against the force with which the hose 100 is pressed against the pump bed 200 by the rotor roller 30. In addition, the restoring force of the hose 100, which primarily depends on its material properties, acts against the force with which the hose 100 is pressed against the pump bed 200 by the rotor roller 30. The pressing force of the rotor roller 30 correspondingly should be dimensioned such that in normal operation the force is sufficient to overcome these counterforces and occludingly press the hose 100 against the pump bed 200. If there is an excessive increase of the flow resistance in the hose portion 140, the fluid pressure in this hose portion 140 rises quickly, whereby the counterforce which acts against the force with which the hose 100 is pressed against the pump bed 200 by the rotor roller 30 is increasing. If the counterforce exceeds the pressing force of the rotor roller 30, the rotor roller 30 is pushed back, whereby the occlusion of the hose 100 is eliminated. In this way, the fluid pressure in the hose portion 140 is limited.

As an alternative embodiment it is also conceivable that charging the piston 25 with positive pressure, but also with negative pressure is realized via the port 23. The port 24 thus can be omitted or thus only serves as connection to a corresponding compensation reservoir or as port 24 provided for maintenance purposes or safety purposes.

As control and/or regulating means a control and/or regulating unit can be provided, which in an advantageous aspect is part of the control and/or regulating unit of the dialysis machine. By means of the control and/or regulating unit the occlusion force can be controlled and/or be adjusted in a step-less and variable manner, in particular corresponding to the demand. In particular, the pressing and/or compression force or the occlusion force can be adjusted in a variable and process-controlled or process-regulated manner via the pneumatic system. Marginal variables, such as the quality of the hose 100, the chosen type of treatment or an inserted filter can also be taken into account. Should the control and/or regulating unit detect a dangerous situation for the patient on the machine side for example with reference to threshold values stored in the memory of the control and/or regulating unit, for example as a result of an abrupt increase in pressure, as is the case for example with a stenosis downstream of the pump, the rotor roller 30 or the rotor rollers 30 is/are positioned by means of the pneumatic cylinder 22 such that the pump pressure is limited to safe values and it is thus prevented that the hose 100 inserted into the peristaltic hose pump bursts or a succeeding filter, such as the dialysis filter, is damaged. In this way, it can also be prevented that a hemolysis of the blood of the patient occurs, since the pump pressure can immediately be limited to safe values.

For the step of inserting the hose 100 into the peristaltic hose pump or of removing the hose 100 from the peristaltic hose pump it can furthermore automatically be provided by means of the control and/or regulating unit that the piston 25 with the rotor roller 30 attached thereto each is completely retracted, so that inserting or removing the hose 100 into or from the peristaltic hose pump advantageously is simplified.

What is claimed is:

1. A peristaltic hose pump for pumping of a medical fluid, comprising:
    a pump bed having an arcuate form; and
    a pump rotor at least partially surrounded by the arcuate form of the pump bed,
    wherein a disposable pump hose is insertable into the pump bed to be located between the pump rotor and the pump bed,
    wherein the pump rotor comprises:
        at least two rotor rollers configured to urge the pump hose against the pump bed, wherein the pump hose is occluded in a region of the at least two rotor rollers, and wherein the medical fluid is pumped through the pump hose by rotation of the pump rotor, and
        at least one actuating device for extending and retracting the at least two rotor rollers hydraulically, pneumatically, or both, wherein the at least one actuating device is a double-acting actuating device, wherein the double-acting actuating device is at least one of a (i) double-acting hydraulic cylinder, (ii) double-acting pneumatic cylinder, (iii) double-acting hydraulic piston, or (iv) double-acting pneumatic piston, to which at least one of a hydraulically generated pressure and a pneumatically generated pressure can be applied on both sides of the cylinder or piston.

2. The peristaltic hose pump according to claim 1, wherein a pressing force, a compression force, or both on the pump hose inserted into the peristaltic hose pump can be generated, adjusted, or both by moving the pump rotor hydraulically, pneumatically, or both by the at least two rotor rollers.

3. The peristaltic hose pump according to claim 1, wherein the double-acting hydraulic cylinder or the double-acting hydraulic piston is actively movable in a first direction and in a second direction.

4. The peristaltic hose pump according to claim 1, wherein the double-acting actuating device is a double-acting hydraulic piston which is actively movable in a first direction and in a second direction by a hydraulically generated positive pressure, a pneumatically generated positive pressure, or both.

5. The peristaltic hose pump according to claim 1, wherein the actuating device is movable in a first direction by a positive pressure and is movable in a second direction by a negative pressure.

6. The peristaltic hose pump of claim 1, further comprising a controller configured to control the pressure applied to the at least one actuating device, wherein the controller is configured to retract the at least two rotor rollers in a parking position allowing at least one of the insertion or removal of the pump hose, and wherein the controller is configured to extend the at least two rotor rollers to urge the pump hose against the pump bed before a pumping operation starts.

7. The peristaltic hose pump of claim 6, wherein the controller is configured to control an occlusion pressure applied by the at least two rotor rollers to the pump hose during the pumping operation.

* * * * *